United States Patent [19]

Kaneoya et al.

[11] Patent Number: 4,851,551
[45] Date of Patent: Jul. 25, 1989

[54] ULTRAVIOLET RAY ABSORBING AGENT

[75] Inventors: Tatsuo Kaneoya, Toyonaka; Haruki Okamura, Osaka, both of Japan

[73] Assignee: Sumitomo Chemical Company, Limited, Osaka, Japan

[21] Appl. No.: 155,699

[22] Filed: Feb. 16, 1988

Related U.S. Application Data

[62] Division of Ser. No. 856,334, Apr. 28, 1986, Pat. No. 4,745,195.

[30] Foreign Application Priority Data

May 2, 1985 [JP] Japan .................................. 60-95105

[51] Int. Cl.$^4$ ........................................... C07D 319/00
[52] U.S. Cl. .................................................... 549/335
[58] Field of Search .......................................... 549/335

[56] References Cited

U.S. PATENT DOCUMENTS

| | | | |
|---|---|---|---|
| 3,766,205 | 10/1973 | Heller et al. | 548/260 |
| 3,948,946 | 4/1976 | Hofer et al. | 549/335 |
| 4,013,619 | 3/1977 | Schmidt | 549/335 |
| 4,414,393 | 11/1983 | Dexter et al. | 548/260 |
| 4,511,491 | 4/1985 | Ishii et al. | 549/335 |
| 4,530,844 | 7/1985 | Smerbeck et al. | 514/258 |
| 4,769,479 | 9/1988 | Sasaki et al. | 549/335 |

FOREIGN PATENT DOCUMENTS 0057160  8/1982  European Pat. Off. ............ 548/260

Primary Examiner—Nicky Chan
Attorney, Agent, or Firm—Stevens, Davis, Miller & Mosher

[57] ABSTRACT

An ultraviolet ray absorbing agent comprising as an active ingredient a spiro compound having a spiro ring structure in the molecule, said spiro compound being represented by the general formula

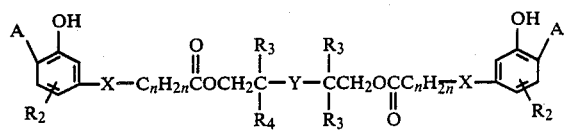

wherein, Y is

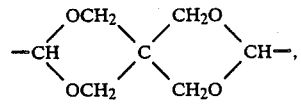

A is

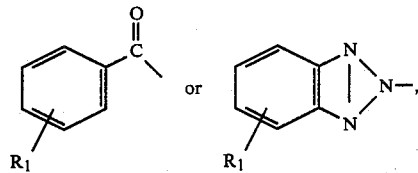

$R_1$ is hydrogen, halogen, lower alkyl of 1 to 4 carbon atoms, lower alkoxyl of 1 to 4 carbon atoms, carboxyl, or sulfo, $R_2$ is hydrogen or alkyl of 1 to 12 carbon atoms, $R_3$ and $R_4$ are alkyls of 1 to 12 carbon atoms, X is methylene, oxygen, imino, sulfur, sulfinyl, or sulfonyl, and n is an integer of 1 to 12.

2 Claims, 1 Drawing Sheet

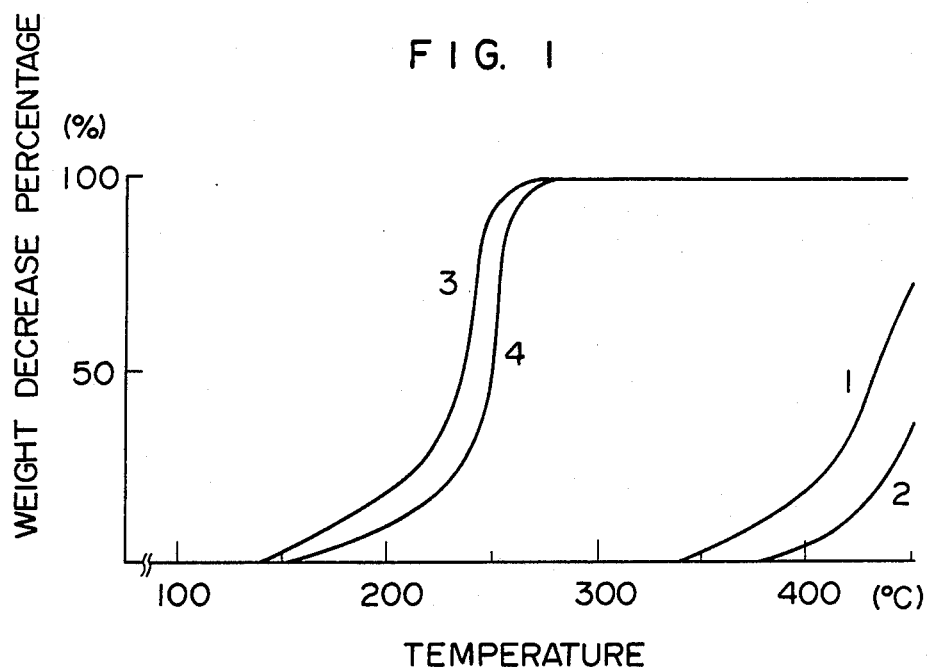

ULTRAVIOLET RAY ABSORBING AGENT

This is a division of application Ser. No. 856,334, filed Apr. 28, 1986, now U.S. Pat. No. 4,745,195.

BACKGROUND OF THE INVENTION

The present invention relates to an ultraviolet ray absorbing agent (UV absorber) comprising a spiro compound specific in structure, as an active ingredient.

Up to now several benzophenone compounds and benzotriazole compounds have been disclosed as UV absorbers and some of them have been commercialized already.

However, these known UV absorbers involve such problems that some of them exhibit low UV absorption power, some are inferior in light resistance, some have colors which will result in color contamination of materials when incorporated thereinto for shielding, and some have low light stability, high sublimability, or low affinity for organic materials. Thus, satisfactory effect has not always been obtained with these UV absorbers.

SUMMARY OF THE INVENTION

Such being the case, the present inventors made intensive studies aiming at development of a UV absorber which will solve the above problems, and as a result were successful in developing spiro compounds of specific structure superior in UV absorptive power, of course, and specially in sublimation resistance (volatility resistance) and heat resistance, and have accomplished the present invention.

According to the invention, there is provided a UV absorber comprising as an active ingredient a spiro compound having a spiro ring structure in the molecule, said spiro compound being represented by the general formula,

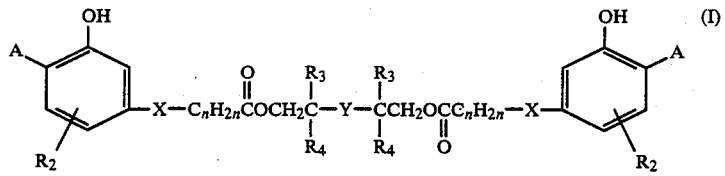

wherein, Y is

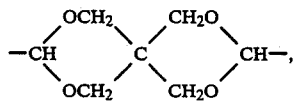

A is

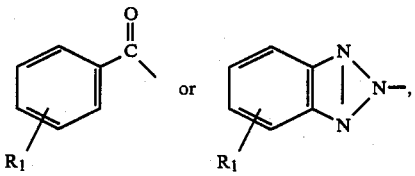

$R_1$ is a hydrogen, halogen, lower alkyl of 1 to 4 carbon atoms, lower alkoxyl of 1 to 4 carbon atoms, carboxyl, or sulfo, $R_2$ is hydrogen or alkyl of 1 to 12 carbon atoms, $R_3$ and $R_4$ are alkyls of 1 to 12 carbon atoms, X is methylene, oxygen, imino, sulfur, sulfinyl, or sulfonyl, and n is an integer of 0 to 12.

BRIEF DESCRIPTION OF THE DRAWING

FIG. 1 shows results of measuring volatilities of different UV absorbers by using a thermobalance, with weight losses (%) as ordinate and heating temperatures as abscissa.

In the FIGURE, the numbers 1 to 4 mean the following compounds:
1: UVA compound No. 1,
2: UVA compound No. 2,
3: Known compound-1,
4: Known compound-2.

DETAILED DESCRIPTION OF THE INVENTION

The spiro compound of general formula (I) above specified according to the invention has the property of absorbing effectively ultraviolet rays of 200 to 400 nm wavelengths which degrade or break down organic substances while not absorbing rays of wavelengths exceeding 400 nm at all, and hence exhibits a strong ultraviolet-shielding action and remarkably less development of color color. Thus the present spiro compound has the superior properties of not only being effective as a UV absorber even when used in a trace amount of about 0.001% by weight of the material to shield but also resulting in no color contamination of the material to shield when used in large amounts. Moreover the present spiro compound is excellent in heat stability (resistance to decomposition and sublimation). None of known benzophenone compounds and benzotriazole compounds surpass the present spiro compound in these properties.

The spiro compound specified according to the present invention can be readily obtained from 3,9-bis(1,1-dialkyl-2-hydroxyethyl)-2,4,8,10-tetraoxaspiro[5,5]undecane represented by the general formula,

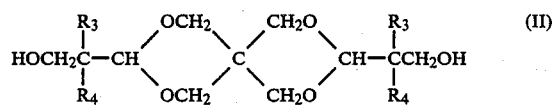

(wherein $R_3$ and $R_4$ have the same meaning as in formula (I)) and an acid derivative or ester derivative of benzophenone or benzotriazole compound represented by the general formula,

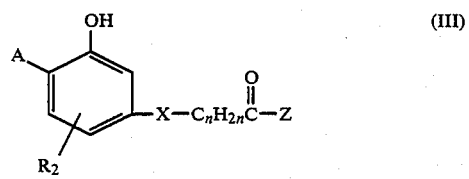

(wherein A, $R_2$, X, and n have the same meaning as in formula (I) and Z is hydroxyl, alkoxyl, or halogen) by reacting them in accordance with the normal esterification method.

Examples of the present spiro compound of general formula (I) are given in Tables I and II.

TABLE 1

Substituent A: $R_1$—⟨benzoyl group⟩

| UVA No. | $R_1$ | $R_2$ | X | $R_3$ | $R_4$ | n |
|---|---|---|---|---|---|---|
| 1 | H | H | O | $CH_3$ | $CH_3$ | 1 |
| 2 | H | H | O | $C_2H_5$ | n-$C_4H_9$ | 2 |
| 3 | H | H | O | $CH_3$ | $CH_3$ | 3 |
| 4 | H | H | O | $CH_3$ | $C_2H_5$ | 1 |
| 5 | H | H | O | $C_2H_5$ | n-$C_6H_{13}$ | 1 |
| 6 | 4-Cl | H | O | $CH_3$ | $CH_3$ | 1 |
| 7 | 4-t-$C_4H_9$ | H | O | $CH_3$ | $CH_3$ | 1 |
| 8 | H | H | O | $CH_3$ | $CH_3$ | 0 |
| 9 | H | H | O | $C_2H_5$ | n-$C_4H_9$ | 0 |
| 10 | H | H | NH | $CH_3$ | $CH_3$ | 0 |
| 11 | H | H | NH | $CH_3$ | $CH_3$ | 1 |
| 12 | H | H | NH | $CH_3$ | $CH_3$ | 2 |
| 13 | H | H | NH | $CH_3$ | $C_2H_5$ | 1 |
| 14 | 4-Cl | H | NH | $CH_3$ | $CH_3$ | 1 |
| 15 | H | H | S | $CH_3$ | $CH_3$ | 1 |
| 16 | H | H | $SO_2$ | $C_2H_5$ | n-$C_4H_9$ | 1 |
| 17 | H | 3'-t-$C_4H_9$ | O | $CH_3$ | $CH_3$ | 1 |
| 18 | H | 5'-$CH_3$ | O | $CH_3$ | $CH_3$ | 1 |
| 19 | 4-Cl | 5'-$CH_3$ | O | $CH_3$ | $CH_3$ | 1 |
| 20 | 4-Cl | 3'-t-$C_4H_9$ | O | $C_2H_5$ | n-$C_{12}H_{25}$ | 1 |
| 21 | 4-$SO_3H$ | 5'-$CH_3$ | O | $CH_3$ | $CH_3$ | 1 |

TABLE 2

Substituent A: $R_1$—⟨benzotriazole group⟩

| UVA No. | $R_1$ | $R_2$ | X | $R_3$ | $R_4$ | n |
|---|---|---|---|---|---|---|
| 22 | H | H | O | $CH_3$ | $CH_3$ | 1 |
| 23 | H | H | O | $C_2H_5$ | n-$C_4H_9$ | 2 |
| 24 | H | H | O | $CH_3$ | $CH_3$ | 3 |
| 25 | H | H | O | $CH_3$ | $C_2H_5$ | 1 |
| 26 | H | H | O | $C_2H_5$ | n-$C_6H_{13}$ | 1 |
| 27 | 4-Cl | H | O | $CH_3$ | $CH_3$ | 1 |
| 28 | 4-$SO_3H$ | H | O | $CH_3$ | $CH_3$ | 1 |
| 29 | 4-t-$C_4H_9$ | H | O | $CH_3$ | $CH_3$ | 1 |
| 30 | H | H | O | $CH_3$ | $CH_3$ | 0 |
| 31 | H | H | O | $C_2H_5$ | n-$C_4H_9$ | 0 |
| 32 | H | H | NH | $CH_3$ | $CH_3$ | 0 |
| 33 | H | H | NH | $CH_3$ | $CH_3$ | 1 |
| 34 | H | H | NH | $CH_3$ | $C_2H_5$ | 1 |
| 35 | 4-Cl | H | NH | $CH_3$ | $CH_3$ | 1 |
| 36 | H | H | S | $CH_3$ | $CH_3$ | 1 |
| 37 | H | H | $SO_2$ | $C_2H_5$ | n-$C_4H_9$ | 1 |
| 38 | H | 5'-$CH_3$ | O | $CH_3$ | $CH_3$ | 1 |
| 39 | H | 3'-t-$C_4H_9$ | O | $C_2H_5$ | n-$C_4H_9$ | 1 |
| 40 | 4-Cl | 5'-$CH_3$ | O | $CH_3$ | $CH_3$ | 1 |
| 41 | 4-Cl | 3'-t-$C_4H_9$ | O | $C_2H_5$ | n-$C_{12}H_{25}$ | 1 |
| 42 | 4-$SO_3H$ | 5'-$CH_3$ | O | $CH_3$ | $CH_3$ | 1 |

The spiro compound specified according to the present invention is effective as a UV absorber for; various high molecular organic compounds including synthetic resins such as polyethylene, polypropylene, polystyrene, polyvinyl chloride, polyvinylidene chloride, MMA resin, ABS resin, polyacrylonitrile, acrylonitrile-styrene copolymer, polyamide, polyester, polyurethane, and polyacetal, synthetic rubbers such as butadiene rubber, isoprene rubber, isoprene-isobutylene rubber, styrene-butadiene rubber, acrylonitrile-butadiene rubber, and ethylene-propylene-(diene) rubber, natural rubber, wool, silk, hemp, and cellulose; and other various organic materials including lubricating oil and other petroleum products, oil and fat, wax, and grease; particularly for high molecular organic compounds.

For using the spiro compound of the present invention as a UV absorber, methods of incorporating conventional UV absorbers are adaptable. Such methods include, for example; that of melt-mixing a powder of the spiro compound with an organic material powder before or during molding; that of blending the spiro compound into a feed monomer in advance of the polymerization thereof; that of adding the spiro compound to a polymer solution, followed by solvent removal; that of blending the spiro compound into an aqueous dispersion of a polymer; and that of impregnating a fibrous polymer with the spiro compound. Also other optional methods are applicable to use the present spiro compound.

When used, two or more of the present spiro compounds may be combined and if necessary, joint use of various common additives is possible which include a softening agent, antioxidant, heat stabilizer, pigment, etc.

When the present spiro compound is used as a UV absorber, its amount can be selected on the basis of objective organic material, properties thereof, the application form and manner thereof, the kind of spiro compound used, etc. Generally speaking, however, the suitable amounts are from 0.001 to 10%, particularly from 0.05 to 5%, by weight based on the objective organic material. Even if used in excessive amounts, the present spiro compound does not produce such unfavorable effect as contamination or coloration of the objective organic material.

As stated above, the present spiro compound is so superior in heat stability (resistance to decomposition and volatility) as to be sufficiently fit for use at high temperatures of 350° C. and higher. Therefore, the present spiro compound can be used advantageously even when organic polymers are processed at high temperatures.

The following examples illustrate the present invention.

PREPARATION EXAMPLE 1

UVA Compound No. 1

A mixture of 3.8 g (0.0124 mole) of 3,9-bis(1,1-dimethyl-2-hydroxyethyl)-2,4,8,10-tetraoxaspiro[5,5]-undecane, 8 g (0.028 mole) of methyl 4-(4-benzoyl-3-hydroxyphenoxy)acetate, and 0.02 g (0.0009 mole) of catalyst lithiumamide was stirred under a nitrogen atmosphere at temperatures of 140°–150° C. for about 3 hours and subsequently under reduced pressures of 4–5 mmHg at the same temperatures for about 4 hours to complete the reaction. Then a suitable amount of toluene was added, the mixture was washed with water and dehydrated, and the toluene was expelled. Subsequent recrystallization from acetone gave a yellow-white powder of the objective compound, yield 8.2 g (81.5%), HPLC purity 99.0%, m.p. 169°–170.5° C.

Anal. Calcd. (for $C_{45}H_{48}O_{14}$) Found: C (%): 66.49, 66.66. H (%): 5.95, 6.06.

PREPARATION EXAMPLE 2

UVA Compound No. 27

A mixture of 4 g (0.013 mole) of 3,9-bis(1,1-dimethyl-2-hydroxyethyl)-2,4,8,10-tetraoxaspiro[5,5]undecane, 9.6 g (0.029 mole) of 2-[2-hydroxy-4-(2'-methoxy-2'-one-ethoxy)phenyl]-5-chlorobenzotriazole, and 0.02 g (0.0009 mole) of catalyst lithiumamide was stirred under a nitrogen atmosphere at temperatures of 140°–150° C. for about 3 hours and subsequently under reduced pressures of 4–5 mmHg at the same temperatures for about 5 hours to complete the reaction. Then a suitable amount of toluene was added, the mixture was washed with water and dehydrated, and the toluene was expelled. Subsequent recrystallization from methyl ethyl ketone gave 9.2 g of a yellow white crystalline powder of the objective compound, yield 78.0%, m.p. 217°–218° C.

Anal. Calcd. (for $C_{48}H_{44}O_{12}N_6Cl_2$) Found: C (%): 56.89, 56.81. H (%): 4.89, 4,92. N (%): 9.26, 9.16. Cl (%): 7.81, 7.81.

EXAMPLE 1

(Thermal coloring test)

About 1.0 g of a UV absorber (UVA) sample is placed in a test tube and heated in an oil bath at 270±5° C. for 30 minutes. After allowing to cool, 500 mg of the sample is dissolved in 50 ml of dioxane (solution A). On the other hand, 500 mg of the untreated sample is dissolved in 50 ml of dioxane (solution B). Solutions A and B are measured for visible ray transmittance at wavelengths of 450, 500, and 550 nm.

Values of $$\frac{T \text{ before heating} - T \text{ after heating}}{T \text{ before heating}} \times 100$$

(T: transmittance)

at 450, 500, and 550 nm are regarded as percentage decreases in transmittance for these wavelengths. With these values, the UVA is evaluated for the degree of thermal degradative coloring. Results of the test are shown in Table 3.

Known compounds 1 and 2 used for comparison are both commercial UV absorbers having the following respective structures:

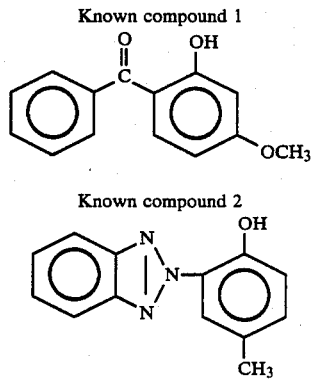

Known compound 1

Known compound 2

TABLE 3

| UVA No. | Percentage decrease in transmittance | | | Rating |
| --- | --- | --- | --- | --- |
| | T 450 nm | T 500 nm | T 550 nm | |
| 1 | 10.1 | 5.4 | 2.5 | — |
| 2 | 10.4 | 5.3 | 2.4 | — |
| 4 | 11.1 | 5.9 | 2.9 | — |
| 5 | 11.3 | 6.0 | 3.1 | — |
| 6 | 10.8 | 5.7 | 2.7 | — |
| 11 | 20.8 | 9.6 | 6.5 | — |
| 14 | 21.9 | 10.2 | 7.8 | — |
| 22 | 11.2 | 6.8 | 2.8 | — |
| 23 | 11.5 | 6.8 | 2.7 | — |
| 25 | 12.0 | 7.0 | 3.2 | — |
| 27 | 12.1 | 7.1 | 3.2 | — |
| 28 | 13.8 | 8.4 | 5.0 | — |
| 32 | 23.1 | 11.5 | 8.0 | — |
| 35 | 23.5 | 11.7 | 8.5 | — |
| 37 | 10.2 | 5.2 | 2.5 | — |
| Known compound 1 | 71.5 | 49.3 | 32.3 | 0 |
| Known compound 2 | 70.9 | 47.5 | 30.2 | 0 |

Note:
The larger number of + marks means the higher heat resistance.

EXAMPLE 2

(Volatility resistance test)

Volatilities of four compounds: UVA compound No. 1, UVA compound No. 2, known compound 1, and known compound 2 were measured by using a thermobalance.

Results of the measurements are shown in FIG. 1.
Measuring method:
 Measuring instrument
 Standard type of desk differential thermobalance (supplied by Raku Denki Co., Ltd.)
 Measurement conditions
 TGA sensitivity: 10 mg
 Rate of heating: 10° C./min
 Chart speed: 8 mm/min
 Recorder sensitivity:
  Heating curve: 20 mV
  Weight loss curve: 10 mV.

EXAMPLE 3

Various UV absorbers were each dissolved in a 25% urethane dope (composed of 25 parts by weight of a polyurethane resin, 3.75 parts by weight of dimethylformamide, and 71.25 parts by weight of tetrahydrofuran) to a concentration as shown in Table 4. Each solution was applied on a nylon film and then dried in an oven at 45° C. for 1 hour to prepare a sheet (10 cm×5 cm). Light resistance tests on the prepared sheets were conducted by Fade-Ometer (supplied by Toyo Seiki Co., Ltd.) irradiation. The darkening degree of each sheet was judged by visual observation. Results thereof are shown in Table 4.

Figures in Table 4 represent darkening degrees of the sheets judged by visual observation on the basis of rating the shade of the unirradiated sheet as 0 and rating that of a thoroughly blackened sheet as 10 to grade the degrees into ten steps according to the blackened degrees.

TABLE 4

| | UVA Compound No. | Addition amount (%) | Degree of darkening by irradiation for a period of | | | |
|---|---|---|---|---|---|---|
| | | | 0 hr | 15 hr | 30 hr | 45 hr |
| Example of present invention | 1 | 1.0 | 0 | 2 | 2-3 | 3 |
| | | 2.0 | 0 | 1 | 1-2 | 2 |
| | 2 | 1.0 | 0 | 2 | 2-3 | 3 |
| | | 2.0 | 0 | 1 | 1-2 | 2 |
| | 4 | 1.0 | 0 | 2 | 3 | 5 |
| | | 2.0 | 0 | 1 | 1-2 | 2-3 |
| | 5 | 1.0 | 0 | 1 | 3 | 4 |
| | | 2.0 | 0 | 0-1 | 2 | 2-3 |
| | 6 | 1.0 | 0 | 2 | 3 | 5 |
| | | 2.0 | 0 | 1 | 2 | 3 |
| | 11 | 1.0 | 0 | 1 | 2 | 4 |
| | | 2.0 | 0 | 1 | 1-2 | 3 |
| | 14 | 1.0 | 0 | 1 | 2-3 | 3-4 |
| | | 2.0 | 0 | 1 | 2 | 2-3 |
| | 22 | 1.0 | 0 | 1 | 3 | 5 |
| | | 2.0 | 0 | 0-1 | 1-2 | 3 |
| | 23 | 1.0 | 0 | 1 | 3 | 5 |
| | | 2.0 | 0 | 1 | 2 | 3-4 |
| | 25 | 1.0 | 0 | 1 | 3 | 5 |
| | | 2.0 | 0 | 0-1 | 1-2 | 3 |
| | 27 | 1.0 | 0 | 1 | 2-3 | 3-4 |
| | | 2.0 | 0 | 0-1 | 2 | 3 |
| | 28 | 1.0 | 0 | 1 | 3 | 4-5 |
| | | 2.0 | 0 | 1 | 2-3 | 3 |
| | 32 | 1.0 | 0 | 1 | 2-3 | 3-4 |
| | | 2.0 | 0 | 0-1 | 2 | 3 |
| | 35 | 1.0 | 0 | 1 | 3 | 5 |
| | | 2.0 | 0 | 1 | 2-3 | 3 |
| Comparative Example | Known compound 1 | 1.0 | 0 | 3 | 5 | 6-7 |
| | | 2.0 | 0 | 2 | 4 | 5-6 |
| | Known compound 2 | 1.0 | 0 | 3 | 5 | 7 |
| | | 2.0 | 0 | 2 | 5 | 6 |
| | None | — | 0 | 5-6 | 6-7 | 8 |

EXAMPLE 4

A dry mixture of 50 parts by weight of an isostatic polypropylene and 0.25 part by weight each of different UVA's was compression-molded in the ordinary way at a temperature of about 204° C. and a pressure of 2,000 psi for 6 minutes to prepare 2.0-mm thick sheets, which were then cut into pieces of 5 cm square. These test pieces (and those similarly prepared without incorporating any UVA) were irradiated in a weather-ometer, and their discoloration degrees were examined. Results of the exmination are shown in Table 5.

TABLE 5

| UVA No. | Irradiation period | | |
|---|---|---|---|
| | 500 hr | 1000 hr | 1500 hr |
| None | Pale yellow | Yellow | Brown |
| 1 | Not discolored | Not discolored | Little discolored |
| 9 | " | " | " |
| 22 | " | " | " |
| 33 | " | " | " |
| Known compound 1 | " | Pale yellow | Yellow |
| Known compound 2 | " | " | " |

The above polypropylene test sheet containing each of UVA Nos. 1, 9, 22, and 23, even after 1000 hour's exposure, gave no indication of embrittlement in a 180° C. bending test and showed neither fine surface cracks nor discoloration. p On the other hand, the sheet containing no UVA and the sheet containing each of known compounds 1 and 2 broke in the bending test after 300 to 400 hour's exposure and after 700 to 800 hour's exposure, respectively.

Tests similar to the above were conducted by using severally a polyethylene resin and a terephthalate resin in place of the polypropylene resin, giving nearly the same results.

EXAMPLE 5

| Polyvinyl chloride (P-1100) | 100 parts by weight |
|---|---|
| Dioctyl phthalate | 50 " |
| KV-33K (Ca—Ba type stabilizer) | 1.5 " |
| Calcium stearate | 0.6 part by weight |
| Barium stearate | 0.2 " |
| Each of different UVA's | 0.1 " |

Mixtures of the above compositions were each kneaded on a 6-inch roll mill at 150° C. for 5 minutes to form 0.5-mm thick sheets. These sheets (and those similarly prepared without incorporating any UVA) were exposed out of doors, and the discoloration-inhibiting effect of each UVA was evaluated by visual observation. Results of the evaluation are shown in Table 6.

TABLE 6

| UVA No. | Irradiation period | | | | |
|---|---|---|---|---|---|
| | 6 months | 12 months | 18 months | 24 months | 30 months |
| None | Yellow tinged | Yellow tinged | Slight dark yellow | Slight dark brown | Dark brown |
| Known compound 1 | Colorless | Colorless | Colorless | Yellow tinged | Yellow tinged |
| Known compound 2 | " | " | " | " | " |
| 1 | " | " | " | Colorless | Colorless |
| 9 | " | " | " | " | Yellow tinged |
| 22 | " | " | " | " | Colorless |
| 33 | " | " | " | " | Yellow tinged |

EXAMPLE 6

A solution composed of 15 parts by weight of an acetylcellulose having an average 2.5 acetoxy groups per one unit of glucose, 0.3 part by weight of UVA No. 1, 2.0 parts by weight of dibutyl phthalate, and 82.7 parts by weight of acetone was spread on glass plates, and the solvent was removed to form films.

These 0.04-mm thick films (and those similarly prepared without incorporating any UVA) were exposed in a Fade-Ometer for 1000 hours, and their embrittlement degrees were examined. The results were as follows:

| UV absorber | Flexural property of film |
|---|---|
| UVA No. 1 | Flexible |
| None | Fragile |

EXAMPLE 7

A fine powder of UVA No. 22 was admixed with a disperse dye for polyester-purposes, to a concentration of 5% by weight, and a Tetron cloth was dyed with the resulting dye composition according to the normal method. The obtained dyeing was improved in light fastness by one or two classes over a dyeing similarly prepared without incorporating any UVA. The same effect is obtainable also by dispersing UVA No. 22 in water using a surfactant and adding the dispersion suitably to a dyeing bath at the time of dyeing. Dyeings of other synthetic fibers can also be improved in light fastness by applying the same or analogous method, that is, by mixing or using the present UV absorber jointly with various dyes or pigments at the time of dyeing the fibers.

EXAMPLE 8

Polyacrylonitrile fibers were treated with 0.03% by weight of UVA No. 29 in a bath ratio of 1:30 at temperatures of 95°-100° C. for 60 minutes, then soaped, rinsed with water, and dried. The light resistance of the fibers themselves was markedly enhanced by this treatment as compared with that of the untreated fibers. In this treatment, it is also possible to use jointly a dye, an optical whitening agent, or an oxidizing agent such as sodium chlorite, whereby the light fastness of the applied dye or optical whitening agent is also improved by one or two classes.

What is claimed is:

1. An ultraviolet ray absorbing compound represented by the general formula,

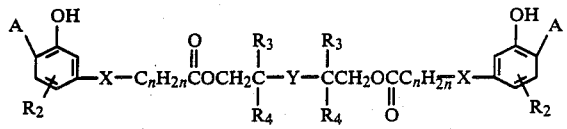

wherein, Y is

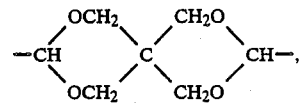

A is

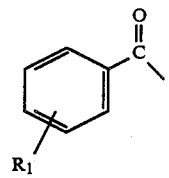

$R_1$ is hydrogen, halogen, lower alkyl of 1 to 4 carbon atoms, lower alkoxyl of 1 to 4 carbon atoms, carboxyl, or sulfo, $R_2$ is hydrogen or alkyl of 1 to 12 carbon atoms, $R_3$ and $R_4$ are alkyls of 1 to 12 carbon atoms, X is methylene, oxygen, imino, sulfur, sulfinyl, or sulfonyl, and n is an integer of 0 to 12.

2. An ultraviolet ray absorbing compound according to claim 1 having the formula,

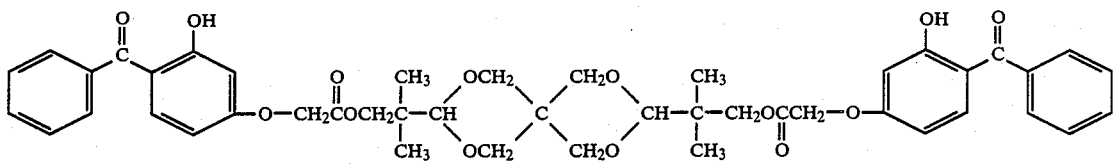

* * * * *